United States Patent [19]

Clayton

[11] Patent Number: 4,795,903

[45] Date of Patent: Jan. 3, 1989

[54] ANALYSIS OF FLUIDS

[75] Inventor: Colin G. Clayton, Tregaron, Wales

[73] Assignee: United Kingdom Atomic Energy Authority, London, England

[21] Appl. No.: 921,498

[22] Filed: Oct. 22, 1986

[30] Foreign Application Priority Data

Oct. 25, 1985 [GB] United Kingdom ............... 8526413

[51] Int. Cl.$^4$ .................... G01N 23/222; G01F 1/00
[52] U.S. Cl. ................... 250/301; 250/356.2; 250/390; 250/270
[58] Field of Search ............. 250/390 C, 301, 270, 250/356.1, 370 C, 370 L, 356.2; 378/53, 46; 376/159, 160

[56] References Cited

U.S. PATENT DOCUMENTS

| | | | |
|---|---|---|---|
| 3,781,556 | 12/1973 | Taylor et al. ................ | 250/390 C |
| 4,057,720 | 11/1977 | Paap et al. .................. | 250/270 |
| 4,228,353 | 10/1980 | Johnson ...................... | 250/356.1 |
| 4,230,945 | 10/1980 | Meir et al. .................. | 250/370 L |
| 4,266,132 | 5/1981 | Marshall, III ................ | 250/359 |

FOREIGN PATENT DOCUMENTS

| | | | |
|---|---|---|---|
| 0007759 | 7/1978 | European Pat. Off. ............ | 250/301 |
| 1124992 | 8/1968 | United Kingdom . | |
| 1566142 | 4/1980 | United Kingdom . | |

Primary Examiner—Carolyn E. Fields
Assistant Examiner—John A. Miller
Attorney, Agent, or Firm—William R. Hinds

[57] ABSTRACT

A method and apparatus are provided for analysing a fluid, especially an oil/water/gas mixture of unknown composition flowing in a pipeline (10). The apparatus can operate remotely, for example on the sea bed. A gamma-ray source (12) and a diametrically arranged scintillator (20) enable the density to be determined; while a fast neutron source (14) and a diametrically arranged germanium gamma spectrometer (22) cooled by a cryo-cooler (26) enable the concentrations of the elements present to be determined. The apparatus also includes a pulsed fast neutron source and a gamma detector to determine the flow velocity of the fluid. The apparatus enables the weight fractions of oil, water and gas to be derived.

7 Claims, 1 Drawing Sheet

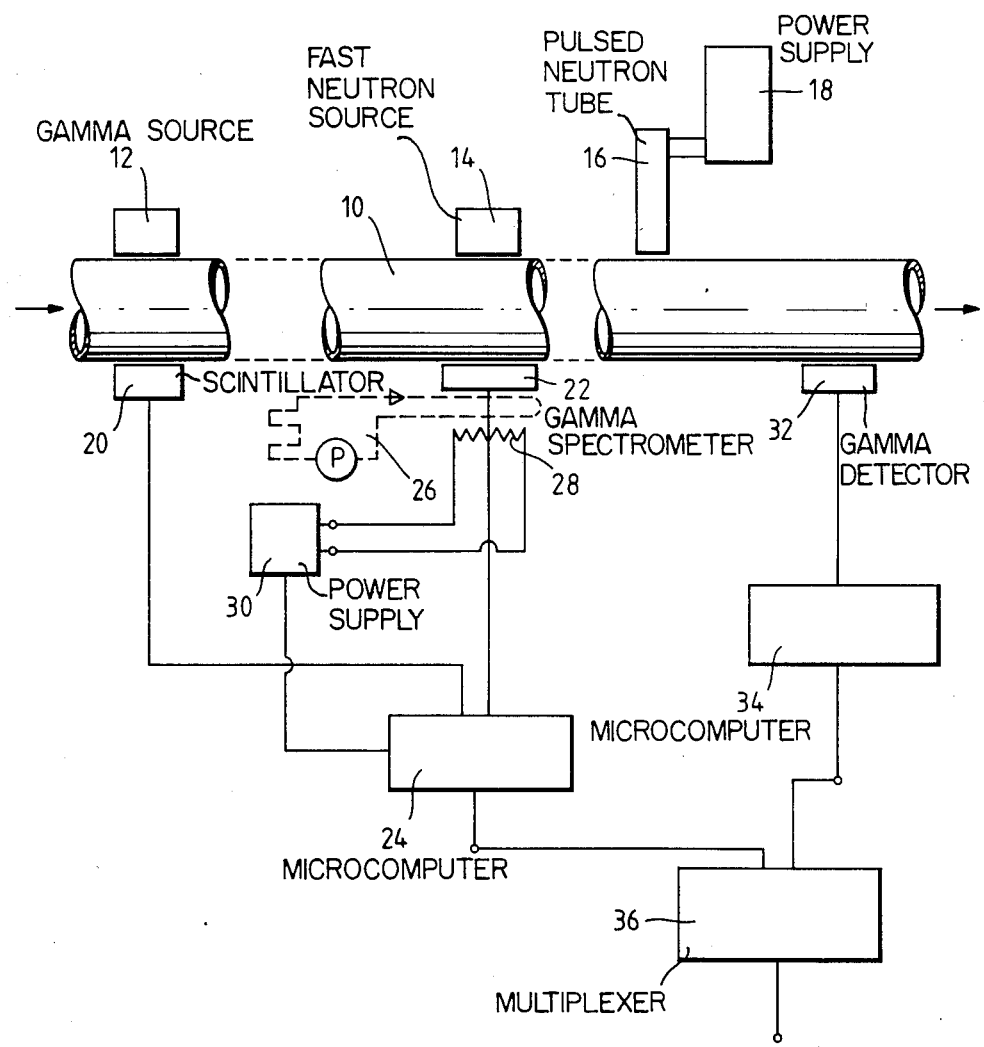

ANALYSIS OF FLUIDS

The invention relates to an apparatus and a method for analysing a fluid, in particular but not exclusively that flowing from an oil well, to determine its density and composition.

The extraction of crude oil from natural reservoirs is normally accompanied by the release of formation water. The relative water output from new wells is usually very low but after a delay, the duration of which is itself of some interest, a significant water content (say 2%) appears. Thereafter this fraction gradually increases to 90% or above. In recent years the use of secondary and tertiary recovery procedures has resulted in a dramatic increase in water content. Thus the fluid emerging from an oil well typically comprises a mixture of crude oil, water, and gas (for example methane).

The management of an oil well requires that the water, oil and gas fractions should all be known and, if separate wells feed into a common pipeline, measurement of the water, oil and gas fractions at each well is required for effective control to be exercised. For example, the output of oil and gas determine the economics of the well, whereas rapid increases in the water content may indicate a need to modify the perforation pattern in the well. The gas to oil ratio is normally constant over a period of years in a water-controlled well, but in a gas-controlled well it can change rapidly, by a factor of more than ten over a period of five years. For under-sea wells the measurement of the water, oil and gas ratios can be made by providing a pipeline from each well to a nearby platform, but this can be expensive. Hence an aim of the present invention is to enable those ratios to be measured at the well-head, even where the well-head is under the sea.

The present invention accordingly provides an apparatus for determining the composition of a fluid which comprises one or more of the constituents oil, water and gas, the apparatus comprising means for measuring the density of the fluid and for generating first electrical signals representative thereof; means for irradiating the fluid simultaneously with fast and thermal neutrons so as to excite atoms of carbon, oxygen and hydrogen in the fluid, and a gamma spectrometer arranged to detect prompt gamma rays emitted by the excited atoms, to determine the intensities of gamma rays of energy 2.2, 4.4, and 6.2 MeV, and to provide second electrical signals representative of those intensities; and means responsive to the said first and second electrical signals for determining, from the said signals and from the stoichiometry of the constituents, the proportions of oil, water and gas in the fluid.

Desirably the invention also provides a pulsed source of very fast neutrons for exciting atoms in the fluid and a detector of gamma rays from the excited atoms arranged so as to determine the flow velocity of the fluid.

The density measuring means preferably comprises a gamma ray source arranged to cause gamma rays to propagate through the fluid, a scintillator arranged to receive the gamma rays, and means to determine from the attenuation of the gamma rays the density of the fluid.

The gamma spectrometer preferably comprises a high-purity n-type germanium spectrometer, and the apparatus includes a heat pump to cool the spectrometer to about 100 K. during operation. Means may also be provided for periodically heating the spectrometer to about 370 K. to anneal it.

An apparatus of the invention may be operated remotely for a year or more, and so may be installed at a remote or under-sea well-head.

The invention also provides a method for analyzing a fluid which comprises one or more of the constituents oil, water and gas, the method comprising irradiating the fluid simultaneously with fast and thermal neutrons so as to excite atoms of carbon, oxygen and hydrogen in the fluid, detecting the intensities of prompt gamma rays of energy 2.2, 4.4 and 6.2 MeV emitted by the excited atoms in the fluid; measuring the density of the fluid; and determining from the said intensities and the density and from the stoichiometry of the constituents, the proportions of oil, water and gas in the fluid.

The invention will now be described by way of example only, and with reference to the accompanying drawings, which shows a diagrammatic view of an apparatus for analysing a fluid in a pipe.

Referring to the drawing, there is shown a 200 mm diameter pipeline 10 through which an oil/water/gas mixture is flowing in the direction of the arrows. Mounted on the outside of the pipeline 10, but spaced apart from each other, are a $^{137}$Cs gamma ray source 12, a $^{241}$Am/Be fast neutron source 14, and a pulsed neutron tube 16 connected to a power supply unit 18. Diametrically opposite the gamma ray source 12 is a sodium iodide scintillator 20; and diametrically opposite the fast neutron source 14 is a high-purity, n-type germanium, high-resolution, gamma spectrometer 22. The gamma source 12 and the scintillator 20 are located by a two-part close-fitting collar (not shown) around the pipeline 10; while the fast neutron source 14 and the spectrometer 22 are located by a similar close-fitting collar (not shown) which excludes sea-water from the region undergoing analysis, and which contains a moderator for the fast neutrons, so as to provide some thermal neutrons. Signals from the spectrometer 22 and the scintillator 20 are supplied to a microcomputer 24. The spectrometer 22 can be cooled, during operation, by means of a heat pump 26 (shown diagrammatically in broken lines) to a temperature of about 100 K. It can also be heated to a temperature of about 370 K., at intervals, by an electric heater 28 connected to a power supply 30 and controlled by the microcomputer 24. A second sodium iodide scintillator 32 is arranged two meters downstream of the neutron tube 16, and is connected to a velocity-calculating microcomputer 34. A multiplex unit 36 receives output signals from the two microcomputers 24 and 34, and transmits that data about every 15 minutes.

Operation of the apparatus is as follows. The $^{137}$Cs gamma source (whose half-life is 30 years) emits gamma rays which pass through the pipeline 10 and its contents. The scintillator 20 provides an indication of the intensity of gamma rays after their passage through the pipeline 10 and its contents, and the attenuation brought about by the pipe contents enables the density of the pipe contents to be determined by the microcomputer 24.

The $^{241}$Am/Be neutron source 14 (whose half-life is over 400 years) emits fast neutrons of energy up to about 10 MeV. The pipeline 10 and its contents are therefore irradiated by fast neutrons and by thermal neutrons, as some of the neutrons are moderated by their passage through the moderator in the collar, and indeed through the pipe wall and the oil/water/gas mixture. Fast neutrons bring about activation of oxygen and carbon atoms by (n, n'γ) reactions, and gamma rays of respective energies 6.2 MeV and 4.4 MeV are consequently emitted. Hydrogen atoms may undergo thermal neutron capture, that is an (n, γ) reaction, with the consequential emission of a gamma ray of energy 2.2 MeV.

The germanium spectrometer 22 is held at a temperature of 100 K. by the heat pump 26 which is based on the Gifford-McMahon closed-cycle cooler. This cryocooler operates in a cyclic thermodynamic process and employs a compressor with an after-cooler heat exchanger which compresses the working gas and then removes the heat of compression, together with an expander with a reciprocating displacer element and a regenerative heat exchanger that removes heat from the spectrometer 22. The intensity of gamma rays of energies 6.2 MeV, 4.4 MeV and 2.2 MeV as detected by the spectrometer 22, along with the known cross-sections for the excitation reactions, enable the elemental concentrations of oxygen, carbon and hydrogen respectively to be calculated by the microcomputer 24. Along with the measured value of density, and the known stoichiometry of the oil and gas, these enable the proportions of oil, water and gas to be determined. This data is provided as an output signal to the multiplex unit 36.

The microcomputer 24 also monitors the energy resolution of the spectrometer 22, which gradually decreases due to the damage caused by the fast neutron flux to which the spectrometer 22 is itself exposed. When it reaches an unacceptably low level, the heat pump 26 is switched off and the power supply 30 energised to heat the germanium spectrometer 22 to about 370 K. for a period of a few tens of hours. This re-anneals the germanium. While re-annealing is being performed no analysis of the pipe contents can be carried out, but re-annealing need only be performed once for several months of operation.

The neutron tube 16 is energised about once every 15 minutes (deuterons being accelerated through 70 kV onto a tritium-in-titanium target) to emit a pulse of very fast neutrons of energy 14 MeV. These irradiate the contents of the pipeline 10, and in particular bring about $^{16}O$ (n,p) $^{16}N$ reactions, for which the threshold energy is 10 MeV. The nitrogen-16 atoms decay with a half-life of a few seconds and emission of gamma rays; the time interval between energising the tube 16, and the detection of a pulse of gamma rays by the scintillator 32 enables the flow velocity of the fluid to be detected. The distance that the scintillator 32 is downstream of the neutron tube 16 is arranged so that, at normal flow-rates, the pipe contents takes about two seconds to flow from the neutron tube 16 to the scintillator 32. The flow velocity is calculated by the microcomputer 34 and provided as an output signal to the multiplex unit 36.

Thus the data transmitted by the multiplex unit 36 consist of the values of density, velocity, and oil/water/gas proportions measured every 15 minutes.

It will be appreciated that because of the long range of neutrons and gamma-rays, the techniques utilized by this apparatus are sensitive to the total volume within pipes having diameters up to about 250 mm so that the problem of achieving a representative sample is largely removed. Except when the highest accuracies are required, the sampled volume is reasonable even when the water is in a non-dispersed state in the oil. Higher accuracies can be achieved if some dispersion of the fluid components can be induced, and for pipes of diameter greater than 250 mm the fluid components must be dispersed to ensure that the sampled volume is representative.

Furthermore, because the fast neutron source 14/spectrometer 22/microcomputer 24 assembly enables elemental concentrations to be derived, the effects of interfering elements, such as carbon in the steel pipe can be allowed for. Measurement of other elements, such as silicon and calcium, can be used to give information on the transmission or build-up of solid material in the pipe. Chlorine, sulphur and nitrogen concentrations can also be derived, if desired.

In a modified form of the apparatus (not shown) two scintillators 32 are provided, spaced along the pipeline 10. The signals from the two scintillators are cross-correlated. This enables the flow velocity to be measured while using a lower intensity neutron pulse from the tube 16, and this can be expected to increase the lifetime of the tube 16.

I claim:

1. An apparatus for determining the composition of a fluid which comprises one or more of the constituents oil, water and gas, the apparatus comprising means for measuring the density of the fluid and for generating first electrical signals representative thereof; means for irradiating the fluid simultaneously with fast and thermal neutrons so as to excite atoms of carbon, oxygen and hydrogen in the fluid, and a gamma spectrometer arranged to detect prompt gamma rays emitted by the excited atoms, to determine the intensities of gamma rays of energy 2.2, 4.4, and 6.2 MeV, and to provide second electrical signals representative of those intensities; and means responsive to the said first and second electrical signals for determining, from the said signals and from the stoichiometry of the constituents, the proportions of oil, water and gas in the fluid.

2. An apparatus as claimed in claim 1 also comprising means for determining the flow velocity of the fluid.

3. An apparatus as claimed in claim 2 wherein the velocity determining means comprises a pulsed source of fast neutrons of energy above 10 MeV arranged to excite atoms in the fluid, and a detector of gamma rays from the excited atoms spaced apart from the said pulsed source in the direction of flow of the fluid, means for measuring the time interval between the emission of a pulse of fast neutrons and the detection of gamma rays by the detector, and means for determining from said time interval and the distance between the source and the detector the flow velocity of the fluid.

4. An apparatus as claimed in claim 1 wherein the density measuring means comprises a gamma ray source arranged to cause gamma rays to propagate through the fluid, a scintillator arranged to receive the gamma rays, and means to determine from the attenuation of the gamma rays the density of the fluid.

5. An apparatus as claimed in claim 1 wherein the gamma spectrometer comprises a high-purity n-type germanium spectrometer, and the apparatus includes a heat pump to cool the spectrometer to about 100 K. during operation.

6. An apparatus as claimed in claim 5 also comprising means for periodically heating the spectrometer to about 370 K. to anneal it.

7. A method for analyzing a fluid which comprises one or more of the constituents oil, water and gas, the method comprising irradiating the fluid simultaneously with fast and thermal neutrons so as to excite atoms of carbon, oxygen and hydrogen in the fluid, detecting the intensities of prompt gamma rays of energy 2.2, 4.4 and 6.2 MeV emitted by the excited atoms in the fluid; measuring the density of the fluid; and determining from the said intensities and the density and from the stoichiometry of the constituents, the proportions of oil, water and gas in the fluid.

* * * * *